(12) United States Patent
Lerf et al.

(10) Patent No.: US 7,998,523 B2
(45) Date of Patent: Aug. 16, 2011

(54) OPEN-PORE BIOCOMPATIBLE SURFACE LAYER FOR AN IMPLANT, METHODS OF PRODUCTION AND USE

(75) Inventors: Reto Lerf, Langendorf (CH); Hans Schmotzer, Birmensdorf (CH); Stephan Siegmann, Pfäffikon (CH)

(73) Assignee: Smith and Nephew Orthopaedics AG, Rotkreuz (CH)

( * ) Notice: Subject to any disclaimer, the term of this patent is extended or adjusted under 35 U.S.C. 154(b) by 227 days.

(21) Appl. No.: 12/092,545

(22) PCT Filed: Oct. 12, 2006

(86) PCT No.: PCT/EP2006/009886
§ 371 (c)(1),
(2), (4) Date: Oct. 6, 2008

(87) PCT Pub. No.: WO2007/051519
PCT Pub. Date: May 10, 2007

(65) Prior Publication Data
US 2010/0004753 A1    Jan. 7, 2010

(30) Foreign Application Priority Data

Nov. 2, 2005  (DE) .......................... 10 2005 052 354

(51) Int. Cl.
*A61L 33/00* (2006.01)
(52) U.S. Cl. ........... 427/2.1; 424/426; 428/623; 427/34; 427/405; 427/419.2; 427/423; 427/216; 427/533; 427/557; 427/576; 427/2.27; 427/2.26; 427/191; 427/226; 427/247; 427/336; 427/352; 228/193; 419/9

(58) Field of Classification Search .................. 427/216, 427/533, 557, 576, 2.27, 2.26; 228/193; 428/623; 424/426; 419/9
See application file for complete search history.

(56) References Cited

U.S. PATENT DOCUMENTS

| 3,605,123 A | 9/1971 | Hahn |
| 3,855,638 A | 12/1974 | Pilliar |
| 4,206,516 A | 6/1980 | Pilliar |

(Continued)

FOREIGN PATENT DOCUMENTS

DE          44 11 974 A1      10/1995

(Continued)

OTHER PUBLICATIONS

Buser, D. et al.: "Influence of Surface Characteristics on Bone Integration of Titanium Implants: A Histomorphometric Study in Miniature Pigs", *J Biomed Mater Res* 25(7):889-901, 1991.

(Continued)

*Primary Examiner* — Michael Barr
*Assistant Examiner* — Andrew Bowman
(74) *Attorney, Agent, or Firm* — Fulbright & Jaworski L.L.P.

(57) ABSTRACT

The invention relates to open-pore biocompatible surface layers for implants, which layers are arranged over virgin surfaces of the implants, wherein pores of the open-pore surface layers are connected to form coherent pore networks and the surface layers have a specific internal surface area of $\geq 0.06$ μm/μm$^2$, preferably $\geq 0.035$ μm/μm$^2$ and especially $\geq 0.025$ μm/μm$^2$, measured by image analysis as a 2D-boundary line per unit of surface area in a metallographic microsection at 100× magnification. The invention further relates to methods of producing such surface layers, to implants coated therewith and to possible uses of the surface layers.

40 Claims, 4 Drawing Sheets

U.S. PATENT DOCUMENTS

| | | | |
|---|---|---|---|
| 4,330,891 | A | 5/1982 | Branemark et al. |
| 4,335,190 | A * | 6/1982 | Bill et al. ............... 428/623 |
| 4,365,359 | A | 12/1982 | Raab |
| 4,542,539 | A | 9/1985 | Rowe, Jr. et al. |
| 4,784,159 | A | 11/1988 | Szilagyi |
| 4,854,496 | A * | 8/1989 | Bugle ............... 228/193 |
| 5,034,186 | A | 7/1991 | Shimamune et al. |
| 5,080,672 | A | 1/1992 | Bellis |
| 5,139,528 | A | 8/1992 | Koch et al. |
| 5,246,530 | A | 9/1993 | Bugle et al. |
| 5,263,986 | A | 11/1993 | Noiles et al. |
| 5,279,831 | A | 1/1994 | Constantz et al. |
| 5,282,861 | A | 2/1994 | Kaplan |
| 5,344,494 | A | 9/1994 | Davidson et al. |
| 5,456,723 | A | 10/1995 | Steinemann et al. |
| 5,603,338 | A | 2/1997 | Beaty |
| 5,807,407 | A | 9/1998 | England et al. |
| 5,817,326 | A * | 10/1998 | Nastasi et al. ............ 424/426 |
| 5,843,289 | A | 12/1998 | Lee et al. |
| 6,008,432 | A | 12/1999 | Taylor |
| 6,025,536 | A | 2/2000 | Bender et al. |
| 6,063,442 | A | 5/2000 | Cohen et al. |
| 6,280,789 | B1 * | 8/2001 | Rey et al. ............ 427/2.27 |
| 6,319,285 | B1 | 11/2001 | Chamier et al. |
| 6,395,327 | B1 | 5/2002 | Shetty |
| 6,419,708 | B1 | 7/2002 | Hall et al. |
| 6,426,114 | B1 | 7/2002 | Troczynski et al. |
| 6,534,197 | B2 | 3/2003 | Noda et al. |
| 6,582,763 | B1 * | 6/2003 | Nishimura et al. ............ 427/216 |
| 6,733,503 | B2 | 5/2004 | Layrolle et al. |
| 6,849,230 | B1 | 2/2005 | Feichtinger |
| 7,074,479 | B2 | 7/2006 | Rogowski et al. |
| 7,258,810 | B2 | 8/2007 | Hunter et al. |
| 7,306,604 | B2 | 12/2007 | Carli |
| 7,306,609 | B2 | 12/2007 | Schmotzer et al. |
| 2001/0031799 | A1 | 10/2001 | Shimp |
| 2002/0143404 | A1 | 10/2002 | Hayashi et al. |
| 2004/0016651 | A1 | 1/2004 | Windler |
| 2004/0030387 | A1 | 2/2004 | Landry et al. |
| 2004/0153154 | A1 | 8/2004 | Dinkelacker |
| 2004/0199261 | A1 | 10/2004 | Jones |
| 2005/0234558 | A1 | 10/2005 | Petersson et al. |
| 2006/0015187 | A1 | 1/2006 | Hunter et al. |
| 2006/0052880 | A1 | 3/2006 | Brosnahan, III et al. |
| 2006/0100716 | A1 | 5/2006 | Lerf et al. |
| 2008/0047931 | A1 | 2/2008 | Fesmire et al. |
| 2009/0012611 | A1 | 1/2009 | Brosnahan, III et al. |
| 2010/0042223 | A9 | 2/2010 | Zinger et al. |

FOREIGN PATENT DOCUMENTS

| | | |
|---|---|---|
| DE | 10022162 A1 | 11/2001 |
| DE | 101 19 096 A1 | 10/2002 |
| EP | 0 523 372 A1 | 1/1993 |
| EP | 1035 230 A1 | 9/2000 |
| EP | 1 062 956 A1 | 12/2000 |
| WO | WO 86/06617 A1 | 11/1986 |
| WO | WO 91/03266 | 3/1991 |
| WO | WO 01/072664 A1 | 10/2001 |
| WO | WO 2006/020090 | 2/2006 |

OTHER PUBLICATIONS

Chang, C. et al.: "Effects of Power Level on Characteristics of Vacuum Plasma Sprayed Hydroxyapatite Coating", *J Therm Spray Tech* 7(4):484-8, 1998.

Hacking, S.A. et al.: "Relative Contributions of Chemistry and Topography to the Osseointegration of Hydroxyapatite Coatings", *Clin Orthop* 405:24-38, 2002.

Lumbikanonda, N. et al.: "Bone Cell Attachment to Dental Implants of Different Surface Characteristics", *Int J Oral Maxillofac Implants* 16(5):627-36, 2001.

Munting, E.: "The Contributions and Limitations of Hydroxyapatite Coatings to Implant Fixation: A Histomorphometric Study of Load Bearing Implants in Dogs", *Int Orthop* 20(1):1-6, 1996.

Nakashima, Y. et al.: "Hydroxyapatite-Coating on Titanium Arc Sprayed Titanium Implants", *J Biomed Mater Res* 35(3):287-98, 1997.

Overgaard, S. et al.: "Improved Fixation of Porous-Coated Versus Grit-Blasted Surface Texture of Hydroxyapatite-Coated Implants in Dogs", *Acta Orthop Scand* 68(4):337-43, 1997.

Overgaard, S. et al.: "Porous-Coated Versus Grit-Blasted Surface Texture of Hydroxyapatite-Coated Implants During Controlled Micromotion: Mechanical and Histomorphometric Results", *J Arthroplasty* 13(4):449-58, 1998.

Søballe, K. et al.: "Bone Graft Incorporation Around Titanium-Alloy- and Hydroxyapatite-Coated Implants in Dogs", *Clin Orthop* 274:282-93, 1992.

Søballe, K. et al.: "Gap Healing Enhanced by Hydroxyapatite Coating in Dogs", *Clin Orthop* 272:300-7, 1991.

Søballe, K. et al.: "Hydroxyapatite Coating Converts Fibrous Tissue to Bone Around Loaded Implants", *J Bone Joint Surg Br* 75(2):270-8, 1993.

Søballe, K. et al.: "Tissue Ingrowth into Titanium and Hydroxyapatite-Coated Implants During Stable and Unstable Mechanical Conditions", *J Orthop Res* 10(2):285-99, 1992.

Søballe, S. et al.: "Hydroxyapatite Coating Enhances Fixation of Porous Coated Implants: A Comparison in Dogs Between Press Fit and Noninterference Fit", *Acta Orthop Scand* 61(4):299-306, 1990.

Tonino, A.J. et al.: "The Hyrdroxyapatite-ABG Hip Syetem: 5- to 7-Year Results from an International Multicenter Study" *J. Arthroplasty* 15(3):274-82, 2000.

Tsui, YC et al.: "Plasma Sprayed Hydroxyapatite Coatings on Titanium Substrates—Part 1: Mechanical Properties and Residual Stess Levels", Biomaterials 19(22):2015-29, 1998.

Tsui, YC et al.: "Plasma Sprayed Hydroxyapatite Coatings on Titanium Substrates—Part 2: Optimization of Coating Properties", *Biomaterials* 19(22)2031-43, 1998.

Wong, M. et al.: "Effect of Surface Topology on the Osseointegration of Implant Materials in Trabecular Bone", *J Biomed Mater Res* 29(12):1567-75, 1995.

U.S. Office Action in co-pending U.S. Appl. No. 10/519,338, mailed Dec. 9, 2008.

U.S. Office Action in co-pending U.S. Appl. No. 10/519,338, mailed Jun. 15, 2009.

U.S. Office Action in co-pending U.S. Appl. No. 10/519,338, mailed Dec. 28, 2009.

Ageorges et al.; "Plasma Spraying of Stainless-steel Particles Coated With an Alumina Shell"; Elsevier Science S. A.; Jul. 17, 2000, 370 (1-2), pp. 213-222.

U.S. Appl. No. 11/722,697, filed Jun. 22, 2007, Zinger et al.

German Examination Report for the German Priority Application No. DE 102 43 101.9 dated Jan. 31, 2003.

International Search Report for PCT Application No. PCT/EP03/05586, mailed Nov. 3, 2003.

Search Report for European Application No. EP 04 03 0665, mailed Jun. 7, 2005.

International Search Report for PCT Application No. PCT/EP2005/013905, mailed Mar. 29, 2006.

International Search Report for related PCT Application No. PCT/EP2006/009886, mailed Jul. 5, 2007 in 12 pages.

European Office Action dated Oct. 30, 2007.

International Preliminary Report for related PCT Application No. PCT/EP2006/009886, mailed Jul. 8, 2008 in 14 pages.

Office Action in co-pending U.S. Appl. No. 10/519,338, mailed Sep. 26, 2007.

Office Action in co-pending U.S. Appl. No. 10/519,338, mailed Apr. 15, 2008.

Chinese Office Action, Application No. 200680041230.6, dated Jan. 24, 2011.

\* cited by examiner

OPEN-PORE BIOCOMPATIBLE SURFACE LAYER FOR AN IMPLANT, METHODS OF PRODUCTION AND USE

CROSS-REFERENCE TO RELATED APPLICATION

This application is a U.S. National Phase of the International Application No. PCT/EP2006/009886 filed Oct. 12, 2006 designating the US and published in German on May 10, 2007 as WO 2007/051519, which claims priority of German Patent Application No. DE 10 2005 052 354.4, filed Nov. 2, 2005.

BACKGROUND OF THE INVENTION

1. Field of the Invention

The invention relates to open-pore biocompatible surface layers for implants and methods of producing such surface layers, and to implants having such surface layers and to the use of such surface layers, as described herein.

2. Description of the Related Art

Implants, and especially joint replacement implants, are becoming ever more important in restorative and curative medicine. In that context, in the case of cementless joint replacement implants, the mechanically stable anchoring of the implant in the bone is of prime importance and is essential for the long-term stability and tolerability of the implants. In this case it is of prime importance that the bone is presented with an optimised joint replacement implant surface so that it can optimally bond to the implant. The surface structure and/or surface coating of a joint replacement implant is/are therefore of crucial importance because they allow—or, in unfavourable cases, prevent or impede—bonding of the bone with the implant or with the implant surface.

For the production of such overgrowth-promoting surface layers, porous layers have hitherto been found to be advantageous. Some methods are known by means of which porous layers can be produced. Materials used in this instance are biocompatible materials, especially metals such as, for example, titanium. The surface layers are arranged, for the most part, on bone implants so that their long-term anchorage in the bone is improved. The porous layers can be produced, for example, by means of a sintering technique, the structures and the sintering conditions being so selected that cavities between the metal or titanium particles applied to the surface are preserved.

With regard to cementless anchoring of joint replacement implants it is possible to differentiate between two types. One type involves bone overgrowth and the other involves bone ingrowth.

Figure 1:
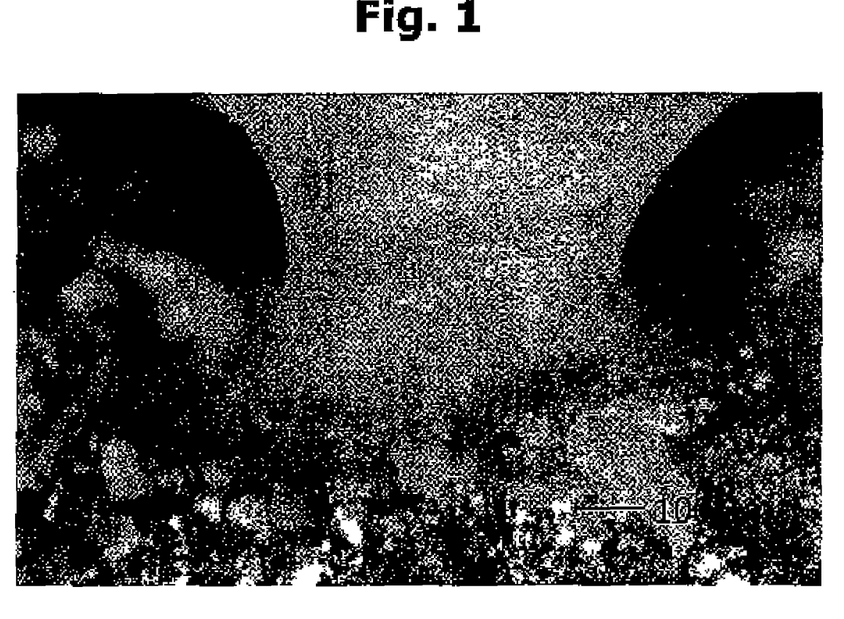
FIG. 1 shows a trebecula which has grown over an implant surface of a Ti6Al7Nb alloy prosthesis roughened by corundum blasting, in accordance with the prior art.

In the case of bone overgrowth, bone cells adhere to the surface. In order for a bone-implant bond of sufficient strength to be produced, the surface must have a certain degree of roughness. Examples of this are implants roughened by means of corundum blasting or vacuum plasma sprayed titanium layers, as are illustrated, for example, in FIG. 1 as prior art. FIG. 1 shows a trabecula which has grown over a blasted surface of a prosthesis composed of a Ti6Al7Nb alloy.

With regard to bone overgrowth for bonding of a bone to an implant, it should be noted that load transmission in the sense of tensile loading is possible only to a very limited extent, since in the event of tensile stress the bone cells are simply lifted off the surface.

Figure 2:
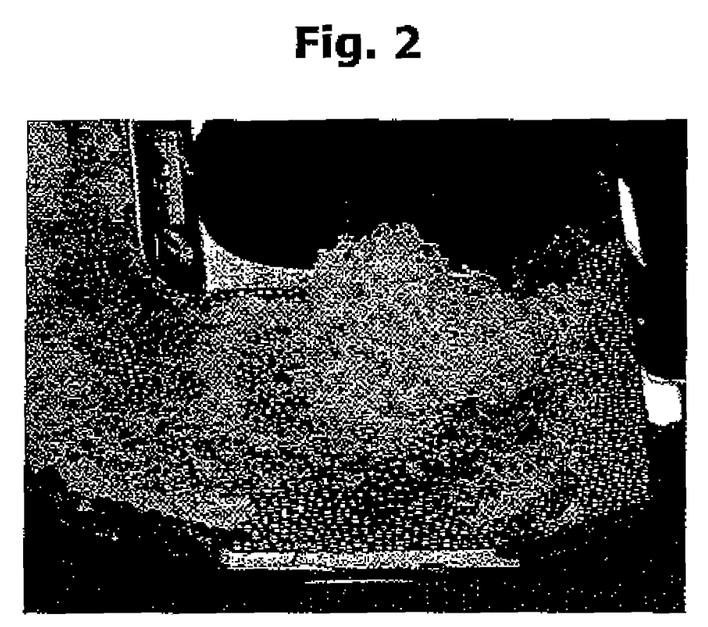
FIG. 2 shows a bead coating of a CoCr alloy with ingrown bone as a macrograph, in accordance with the prior art.

In the case of bone ingrowth, bone grows into cavities on and/or at the surface of the implant. Examples of such surfaces are open-pore sphere or wire surfaces, which can be produced, for example, by means of a sintering technique. Examples are to be widely found of the former, sphere surfaces are those referred to as bead coatings. Such a coating is shown in FIG. 2, which shows a macrograph of a bead coating of a CoCr alloy with a bone grown into it.

Nevertheless, in many cases, stable growth of bone over such an implant surface does not, however, occur. Furthermore, ingrowth into such a sphere or wire surface, enabling tensile forces also to be transmitted to a certain extent by virtue of an interlocking of the bone with the surface which occurs on a sphere or wire surface, requires distinctly more time than bone overgrowth.

Various methods with which surfaces for bone overgrowth can be produced are known from the literature.

V. Galante et al., JBJS, 53A (1971), pages 101-114 describes, for example, the sintering of a mesh of fine titanium wires onto a substrate.

The two U.S. Pat. Nos. 3,855,638 and 5,263,986 disclose a method wherein a titanium powder composed of spherical particles of various sizes is sintered onto a substrate.

U.S. Pat. No. 4,206,516, on the other hand, uses a ground titanium hydride powder composed of angular particles, which again is sintered onto a substrate.

By means of those methods it is possible to produce open-pore layers into whose pores bones are able to grow. Those porous structures made by means of a sintering technique can be produced by controlling the sintering conditions, it being possible to obtain cavities between the titanium particles applied to the surface of the substrate.

It is furthermore possible by means of sintering to produce a skeleton of titanium from a mixture of thermally unstable position-retainers and titanium powder or of position-retainers and titanium hydride powder. Methods in that regard are described, for example, in the Patent specifications U.S. Pat. No. 5,034,186 or WO 01/19556; likewise, a method of the company Intermedics, Austin, USA entitled "Cancellous Structured Titanium" addresses such a possibility.

Figure 3:
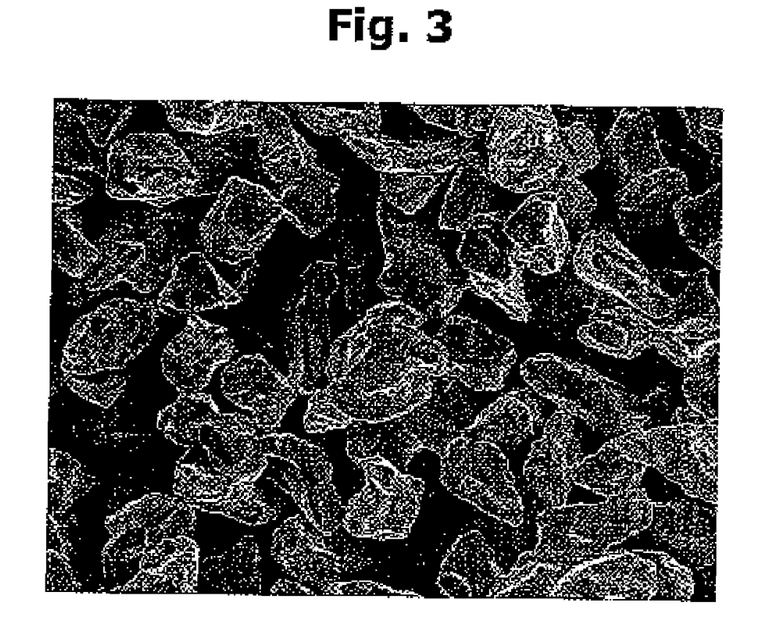
FIG. 3 is a scanning electron micrograph at 50× magnification of a titanium coating produced by means of a sintering process, in accordance with the prior art.
Figure 4:
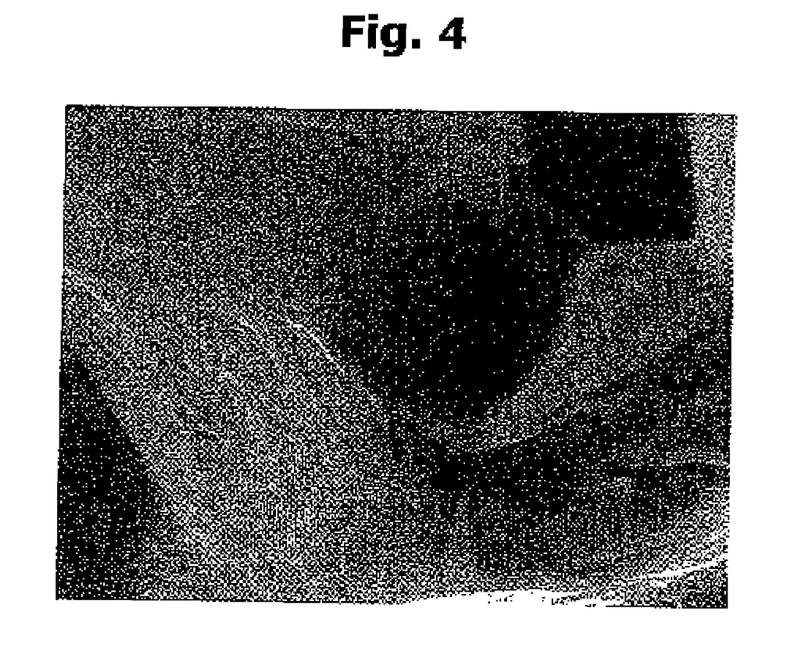
FIG. 4 shows the titanium coating of FIG. 3 at 1000× magnification.

However, in all titanium layers produced by a sintering process of such a kind it is inherently disadvantageous that the roughness of the erstwhile titanium particles or titanium fibres is smoothed out as a result of surface diffusion. Even though the bone can grow into the pores, it is scarcely possible for the bone cells, on a microscopic scale, to gain any hold on the smooth titanium surface. That situation is illustrated in FIGS. 3 and 4, FIG. 3 showing a scanning electron micrograph of a titanium coating produced in accordance with the above-mentioned U.S. Pat. No. 4,206,516 at 50× magnification. FIG. 4 also shows a scanning electron micrograph of the same titanium coating, but at 1000× magnification. The surface smoothed out at the microscopic level by surface diffusion can clearly be seen.

That disadvantage can be avoided by dramatically reducing the time for which the titanium particles are exposed to high temperatures.

Various methods with which surfaces for bone overgrowth can be formed are known from the literature. As already mentioned, thermal spraying processes, notably vacuum plasma spraying, form a possible way of producing a rough titanium surface industrially. The process parameters can be so selected in thermal spraying that the particles of a layer material are heated only briefly, being at most partially melted and being rapidly quenched on meeting the substrate. As a result of the method being performed in that way, the rough surface of the spray powder is preserved to some extent and results in a visible topographical roughness of the sprayed layer. Solutions in that regard for producing a rough surface are described, for example, in U.S. Pat. No. 4,542,539, or in the articles in AESCULAP, Wissenschaftliche Information 22: "Die PLASMAPORE-Beschichtung für die zementlose Verankerung von Gelenkendoprothesen" ["The PLASMAPORE coating for cementless anchoring of joint endoprostheses"] and in "Osteointegration, Oberflächen- und Beschichtungen orthopädischer Implantate für den zementfreien Einsatz" ["Osteointegration, surfaces and coatings of orthopaedic implants for cementless use"] of PI Precision Implants AG.

Figure 5:
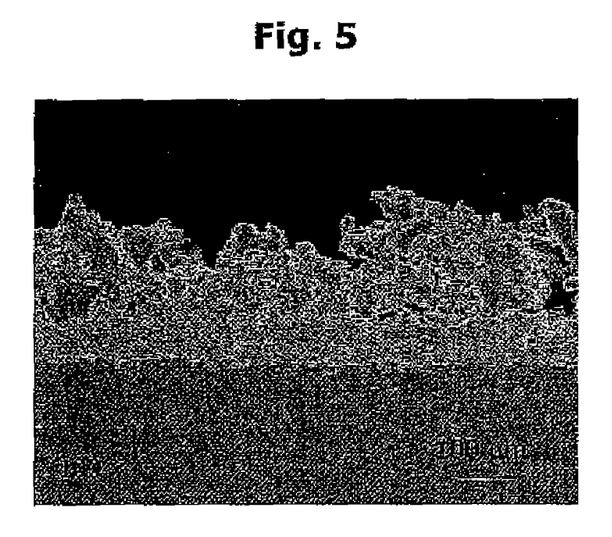
FIG. 5 shows a metallographic microsection through a vacuum plasma sprayed titanium layer at 100× magnification with good visualisation of a high degree of roughness, but with few cavities present.

The gain in roughness that can be achieved with the vacuum plasma spraying method is, however, offset by a serious disadvantage, since flame-sprayed or plasma-sprayed titanium layers generally have virtually no pores that are open to the outside and they consequently prevent ingrowth of the bone per se. Nor has it been possible for those disadvantages to be overcome by the methods mentioned in the above-mentioned references. An example of a titanium layer applied by means of vacuum plasma spraying is illustrated in FIG. 5. That Figure shows a metallographic microsection through a vacuum plasma sprayed titanium layer as a scanning electron micrograph at 100× magnification. The roughness of the titanium layer applied to the substrate can be seen clearly.

In addition, other methods are known which produce, by chemical or electrochemical means, a rough surface over which bone can grow better. The methods involved are etching or anodising methods, which are described, for example, in P.-I. Branemark et al., DE 300 74 46 C3 or in S. Steinemann et al., U.S. Pat. No. 5,456,723.

Whereas the techniques thus far presented were geared either to bone overgrowth or to bone ingrowth, there are recent developments which allow the two cementless types of anchoring in the bone to be combined. Such a surface is known, for example, under the tradename Hedrocel® or "Trabecular Metal". Hedrocel® is a surface by means of which anchoring of the bone is possible. The production of that surface is, however, very elaborate and expensive. Starting with a highly porous foam of carbon glass, an open-pore tantalum structure is obtained by depositing tantalum onto a carbon glass framework in a chemical vapour deposition ("CVD") process. To apply that porous structure to a surface of a bone implant, a further CVD process is required, in which the processing temperature is more than 900° C. which may lead to impairment of the structure of the substrate, that is, of the load-bearing implant. The two-step production process of the Hedrocel® surface is described in the specifications of R.B. Kaplan, U.S. Pat. No. 5,282,861 and R.C. Cohen et al., U.S. Pat. No. 6,063,442.

A further method, which is described in European Patent Application EP 1 449 544 A1, is directed to subsequently roughening the surface of sintered particles. That roughening operation is performed by means of a wet-chemical etching process, and therefore the production of the roughened surface again results in a two-step method, namely previous application of sintered particles to a substrate and subsequent wet-chemical etching. That method also holds the danger that undesired, and indeed often dangerous, residues from the etching process will remain in the pores of the applied surface layer.

Other technologies are aimed at additionally providing porous layers such as those produced, for example, by a sintering technique with a very thin substance that promotes bone overgrowth. That substance is frequently hydroxyapatite, that is, the mineral constituent of bone. A method of that kind is described, for example, in U.S. Pat. No. 5,279,831, with application to surfaces that have already been made porous being explicitly claimed therein. U.S. Pat. No. 6,426,114 describes the application of such a coating by means of a sol-gel process. As a general rule, the hydroxyapatite layers so obtained are less than 1 µm thick and can therefore be applied to any desired surface, including, therefore, a porous surface.

In accordance with the above, it can be stated in summary that there have hitherto been many different attempts at producing, on a joint replacement implant, a surface that is structured in a satisfactory manner for the ingrowth of bone. It has, however, hitherto been possible merely

- to produce open-pore coatings into which the bone can grow but which, in the sub-micrometer range, do not provide any topographical stimuli for osteoblast adhesion and consequently for the overgrowth of bone in a manner which is rapid or better than the prior art;
- to make available a surface method which provides a roughness of a few micrometers and a sub-micrometer structure for better adhesion of the osteoblasts, but those surfaces do not have an open pore structure into which the bone could grow;
- to produce coatings having a high degree of roughness in the region of a few tens of micrometers, which have a limited degree of porosity but which again do not actually have a suitable, i.e. sub-micrometer, structure;
- to produce open-pore coatings into which the bone can grow and whose surface has sub-micrometer roughness but which do not have a sufficiently high degree of macro-roughness and which consequently cannot "grab onto" the bone.

SUMMARY OF THE INVENTION

An objective of the present invention is accordingly to fill the afore-mentioned gap, a problem addressed by some embodiments of the invention being to form the surface of a joint replacement implant in such a manner that the surface has stable cavities which are open to the outside and which are of a sufficient size that vascularized bone tissue can grow in, the surface having very good biocompatibility in the sense of having a bioinert or slightly bioactive property, and also a specifically adjustable sub-micrometer sizing, which can provide anchoring points for the osteoblasts, the production of the surface being possible in a simple and one-step method and a substrate to be coated being subject to only slight thermal load.

A further problem addressed by some embodiments of the invention is to make available an implant having such a surface layer and the use thereof.

These problems are solved by an open-pore biocompatible surface layer, by methods of producing it, by an implant having the surface layer and by the use of the surface layer described herein.

One problem addressed by some embodiments of the invention is especially solved by an open-pore biocompatible surface layer for an implant, which is arranged over a virgin surface of the implant, wherein pores of the open-pore surface layer are connected to form a coherent (e.g., unified) pore network and the surface layer has a specific internal surface area of $\geq 0.06$ µm/µm², preferably $\geq 0.035$ µm/µm² and especially $\geq 0.025$ µm/µm², measured by image analysis as a 2D-boundary line per unit of surface area in a metallographic microsection at 100× magnification.

One important aspect of some embodiments of the invention is that the open-pore biocompatible surface layer has a pore network whose pores are constructed to be coherent also within the layer, with the result that bone tissue growing into the surface layer can completely penetrate the pore network and in that manner forms a bone structure that traverses the pore network and which extends, inter alia also within the surface layer, into channels of the surface layer forming the pore network. In that manner, the ingrowing bone tissue travels through and under the surface of the surface layer and the coherent pore network in a manner that ensures intimate bonding of the surface layer with the bone tissue and prevents detachment of the bone tissue from the surface layer, for example under tensile load.

A further important aspect of an embodiment of the invention is the internal structuring of the surface layer and its large internal surface area, which exhibits a high degree of roughness, with the result that overgrowth of bone tissue over that surface is additionally promoted. It should be mentioned at this point that of course the external surface of the surface layer also has such a degree of roughness.

The combination of a surface layer having a large internal surface area with the coherent pore network according to some embodiments of the invention formed within the open-pore surface layer ensures optimized bonding of a bone to the surface layer, the tissue thereof growing into the surface layer and extending inter alia to a great extent also into channels of the pore network that run beneath the surface of the surface layer.

Accordingly, the surface layer according to some embodiments of the invention has stable cavities which are open to the outside, which have a size such that vascularized bone tissue can grow in and the average diameter of which is in the region of approximately 200 µm.

In accordance with one embodiment of the invention, at a distance of 300 µm from the virgin surface of the implant, the surface layer has a shear force of ≧350 N, preferably ≧500 N and especially ≧1000 N (measured in accordance with S. Siegmann, M. Dvorak, H. Grützner, K. Nassenstein and A. Walter: Shear testing for characterizing the adhesive and cohesive coating strength without the need of adhesives; Proceedings of ITSC 2005 Thermal Spray connects: Explore its surfacing potential! (2005), p. 823-829, ISBN 3-87155-793-5).

Furthermore, cutting work required to shear off the layer at a distance of 300 µm from the virgin surface of the implant is ≧0.01 J, preferably ≧0.05 J and especially ≧0.1 J.

In addition, relative abrasion of the surface layer at a porosity of 40%-50% and at a layer thickness of 0.7 mm-1.0 mm, measured on the basis of the Miller test in accordance with ASTM G75-01 without abrasion medium, is ≦0.1 mg/min, preferably ≦0.05 mg/min and especially ≦0.01 mg/min.

Figure 6:
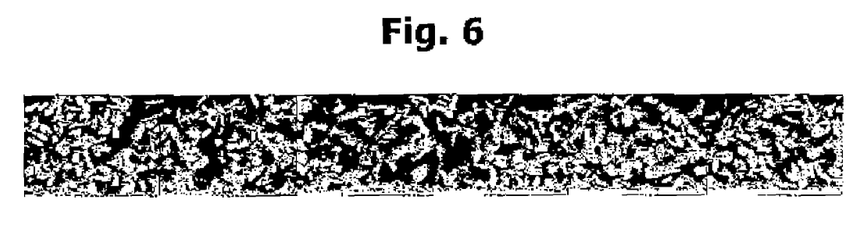
FIG. 6 shows a metallographic microsection through a vacuum plasma sprayed titanium layer according to an embodiment of the invention at 20× magnification.

In addition, the surface layer exhibits both a connection of the particles forming the surface to one another and a connection of the particles to the substrate, that is, to the virgin surface of the implant, which is referred to as a sinter neck. The average diameter of the sinter necks of the surface layer according to some embodiments of the invention is ≧5 µm, preferably ≧15 µm, and especially ≧25 µm. A micrograph section of such a kind is illustrated, for example, in FIG. 6. In that Figure, both the nature and the dimensions of those sinter necks can be seen clearly. The above-mentioned dimensions of the sinter necks were determined quantitatively by measuring the thinnest cross-section. As an example, values of 39 µm±16 µm were measured in that procedure.

According to some embodiments of the invention, the thickness of the surface layer is in the range from 0.1 mm to 2.5 mm, preferably in the range from 0.3 mm to 1.9 mm and especially in the range from 0.5 mm to 1.5 mm.

The maximum pore diameter is in the range from 10 µm to 800 µm, preferably in the range from 50 µm to 600 µm and especially in the range from 100 µm to 400 µm.

According to some embodiments of the invention, the pore mouth of the pores, that is, the opening thereof to the outside, is in the range from 10 µm to 900 µm, preferably in the range from 75 µm to 680 µm and especially in the range from 150 µm to 500 µm.

The porosity of the surface layer is in the range from 20% to 85%, preferably in the range from 30% to 70% and especially in the range from 40% to 50%, it being emphasized once more that the coherent pore network extends up to the virgin surface of the implant and/or an optional intermediate layer which can be arranged between the surface layer according to some embodiments of the invention and a virgin surface of the implant.

In accordance with a preferred embodiment of the invention, the surface layer is formed from, preferably angular, titanium particles that are coated, especially compounded, with silicon particles. The quantity of silicon particles used for compounding is in the range from 0.5% by weight to 8.5% by weight±1.5% by weight, preferably from 0.5% by weight to 3.0% by weight, and especially 1.0% by weight±0.5% by weight.

The titanium particles used according to some embodiments of the invention are preferably a titanium powder whose particles have a particle size in the range from 90 µm to <200 µm, preferably in the range from 150 µm to <200 µm. The silicon particles used are preferably silicon powder having a particle size of ≦80 µm, preferably ≦40 µm and especially ≦20 µm, so that titanium particles coated with silicon particles are in the form of compound particles having an axial ratio of ≦5:2. The particle size distribution measured in percentage by volume with respect to the particle size in accordance with ISO/DIS 13322-1 is given in the following Table:

| particle size distribution [% by vol.] | particle size [µm] |
|---|---|
| D10 | 90-149 |
| D50 | 150-229 |
| D90 | 230-330 |

The titanium particles coated with silicon particles, which are in the form of compound particles, have a particle size of ≧90 µm, preferably ≧150 µm, with the particle size distribution defined above being adhered to.

In accordance with a preferred embodiment, an intermediate layer is provided between the virgin surface of the implant and the surface layer. Such an intermediate layer is advantageous, for example, when the basic material of the substrate to be coated is not immediately suitable for coating by means of vacuum plasma spraying, or when an extremely high strength is required which is governed, for example, by the particular application. In that case, the virgin surface of the implant can first be covered with an impermeable base layer preferably consisting of a bioinert material which is preferably a metal. Titanium is preferred as the metal on account of its bioinert properties and its very high strength and low relative density. Silicon or titanium compounded with silicon also comes into consideration, however. Other bioinert metals such as, for example, tantalum, platinum or other noble metals also come into consideration as base layer materials.

The intermediate layer has a layer thickness of ≦200 µm, preferably ≦100 µm and especially in the range from 30 µm to 50 µm.

In accordance with a further embodiment of the invention, bioactive particles, especially of titanium dioxide and/or calcium phosphate, preferably hydroxyapatite and/or tricalcium phosphate, are also arranged on the surface layer. The bioactive particles have a particle size in the range from 0.01 µm to 5 µm, preferably in the range from 0.1 µm to 3 µm and especially in the range from 0.2 µm to 1 µm, it also being possible in special cases for particles of ≦0.01 µm to be used. Those powders can be applied by means of sol-gel processes using a water-based or silicate-based binder, by means of precipitation or by means of electrophoresis, there being no restrictions as far as the method of application is concerned and it being possible for all of the established and/or suitable application procedures to be used.

By means of the surface layer according to some embodiments of the invention, therefore, the possibility is provided of ensuring optimum anchoring of a bone to and in an implant or its surface layer, resulting in bone ingrowth and bone overgrowth. The surface layer according to some embodiments of the invention, which is optionally bonded to a virgin surface of the implant in an optimum manner by way of an intermediate layer imparting stability and strength, makes it possible to provide a bone anchor that can be produced in a simple and one-step method and for which the basic material of the implant is subjected to only very little thermal load.

Since the surface layer is formed from individual metal particles bonded to one another, variation of the nature and size or dimensioning of the metal particles can readily be adapted to the particular properties desired, since the particles are applied layer by layer and are bonded to one another by means of a thermal process. In that manner, it is possible to produce a surface having very good biocompatibility in the sense of having a bioinert or slightly bioactive property, which has an inherently large internal surface area and very good mechanical strength and stability and which also exhibits only extremely little wear with respect to abrasion, even under abrasive stress, and which therefore decisively increases and improves the service life and comfort of implants, especially compared with the current state of the art.

Furthermore, a problem addressed by some embodiments of the invention is solved by a method of producing an open-pore biocompatible surface layer for an implant, especially a joint replacement implant, wherein the following steps are carried out:

coating, especially compounding, of titanium particles with an additive, especially sintering adjuvant, that forms with titanium or an alloy thereof a eutectic that melts at a lower temperature than pure titanium, to produce compound particles, application of at least one layer of compound particles to a virgin surface of the implant by means of a vacuum plasma spraying method, to produce a surface layer on the implant.

The problem is further solved by a method of producing an open-pore biocompatible layer for an implant, especially a joint replacement implant, wherein the following steps are carried out:

application of at least one layer of titanium particles to a virgin surface of the implant by means of a vacuum plasma spraying method, to produce a surface layer on the implant, production of an arc between the virgin surface of the implant, especially the surface layer on the implant, and a counter-electrode.

The problem is moreover solved by a method of producing an open-pore biocompatible surface layer for an implant, especially a joint replacement implant, wherein the following steps are carried out:

coating, especially compounding, of titanium particles with an additive, especially sintering adjuvant, that forms with titanium or an alloy thereof a eutectic that melts at a lower temperature than pure titanium, to produce compound particles, application of at least one layer of compound particles to a virgin surface of the implant by means of a vacuum plasma spraying method, to produce a surface layer on the implant, production of an arc between the virgin surface of the implant, especially the surface layer on the implant, and a counter-electrode.

According to some embodiments of the invention, the arc can be formed between the virgin surface of the implant, or a surface layer present on the implant, and a counter-electrode directly during application of the titanium particles and/or compound particles to the implant; alternatively, however, the arc can be formed after application of the titanium particles and/or compound particles. A further alternative is to use the arc process during and after application of the titanium particles and/or compound particles.

In the first case, that is, in the case of simultaneous application of the particles and use of the arc, in addition to the internal, plasma-forming circuit of the coating method a second circuit can be connected between the plasmatron or plasma gun and the component so that a transferred arc can be established via the electrically conductive plasma. To produce the arc, rather than producing it from the plasmatron or spray gun, it is also possible to produce it by means of an available counter-electrode.

The use of an arc during or after application of titanium particles and/or compound particles to a virgin surface of an implant has the significant advantage of Joule heating at high contact resistances, that is, in this case at the contact points between the titanium particles and/or compound grains or particles, since these constitute restricted sites and hence produce an increased electrical resistance. In addition to this, especially in the case of compound particles, the covering layer of sintering adjuvant on the titanium particles coated therewith produces a higher resistance than the titanium particles themselves, with the result that here too Joule heating is produced which leads to localised heating confined solely to the points of contact of the grains, especially in the covering layer, which heating strengthens the sinter necks connecting the particles.

In summary, that heat which is liberated there and then leads to additional, localised sintering and consequently to a strengthening of the sinter necks between the titanium particles without, however, causing at the same time sintering and/or smoothing out of the remaining regions of the particles and the substrate surface. That advantageous effect produces in the coating a great increase in the shear strength thereof by a factor of 2 to 3 compared with the same coating parameters in the production process but without a transferred arc. Compared with conventional coating methods, a six- to seven-fold increase in shear strength compared with a purely open-pore titanium layer can be achieved by the combined use of a sintering adjuvant and a transferred arc.

It should be mentioned at this point that an arc is to be understood as being any kind of energy effect, in particular of an electrical nature, by which a Joule heating effect can be achieved at restricted sites. A significant advantage of the use of an arc is, however, that it can be applied directly during application of the titanium particles and/or compound particles, with the result that the coating process is ultimately a one-step process and does not require an additional process step, although subsequent strengthening of the sinter necks by application of an arc is possible.

It should otherwise be pointed out that the contact resistance caused by the sintering adjuvant can be influenced according to some embodiments of the invention by the choice of sintering adjuvant and by its layer thickness, and therefore a specific, very high consolidation of the open-pore surface layer with a coherent pore network can be achieved.

In accordance with some embodiments of the invention, silicon or cobalt are used as sintering adjuvant and, in the case where silicon is used, preferably silicon particles are used in a quantity in the range from 0.5% by weight to 8.5% by weight ±1.5% by weight, preferably from 0.5% by weight to 3.0% by weight and especially 1.0% by weight ±0.5% by weight.

Furthermore, the titanium particles used are an angular titanium powder having a particle size in the range from 90 μm to <200 μm, preferably in the range from 150 to <200 μm, which has preferably been ground and, in accordance with some embodiments of the invention, preferably produced via the hydride stage.

The silicon particles used are silicon powder having a particle size ≦80 μm, preferably ≦40 and especially ≦20 μm. Regarding the particle size distribution, attention is drawn to the foregoing remarks.

The titanium particles are coated with silicon particles in such a manner that the coated titanium particles, then referred to as compound particles, have a particle size ≧90 μm, preferably ≦150 μm, it being necessary once again to take account of the particle size distribution defined hereinbefore.

Owing to those size ratios it is possible to coat the titanium particles with silicon particles and in that manner provide a large surface area which, when subsequently melted during a vacuum plasma coating process, is available for the bonding of particles and for the bonding of particles to a substrate.

Furthermore, adhering to the above-mentioned particle sizes, it is possible to coat titanium particles with silicon particles in such a manner that an angular periphery of the coated titanium particles, that is, of the compound particles, is substantially preserved and the compound particles have an axial ratio of ≦5:2.

In addition, the parameters of the vacuum plasma spraying method are adjusted in such a manner that the compound particles are caused to start to melt only superficially and, on meeting the virgin surface of the implant, or the intermediate layer if present, are only slightly compacted, so that their original geometry, especially as regards their axial ratio, is to a great extent preserved. In that manner it is possible, by means of the angular particles which meet a substrate surface, to form a structure that is joined together substantially only by points and edges of the individual angular particles, so that a kind of cage is produced from which the coherent pore network is formed and through whose cavities bone substance is able to grow over and grow in.

As mentioned before, it is possible for the virgin surface of the implant to be coated, prior to a coating operation with compound particles, with a base layer, that is, with an intermediate layer which can be constructed according to the basic material of a virgin implant body and which preferably consists of pure titanium and/or of titanium coated with silicon.

In accordance with a preferred embodiment, application of the intermediate layer takes place in the same vacuum plasma spray coating operation as the application of the actual surface layer, the application of the intermediate layer taking place before the application of the surface layer.

The base or intermediate layer is produced with a layer thickness of ≦200 μm, preferably ≦100 μm and especially in the range from 30 μm to 50 μm.

It is otherwise provided according to some embodiments of the invention that bioactive particles, especially of titanium dioxide and/or calcium phosphate, preferably hydroxyapatite and/or tricalcium phosphate, having a particle size in the range from 0.01 μm to 5 μm, preferably in the range from 0.1 μm to 3 μm and especially in the range from 0.2 μm to 1 μm, are applied to the surface layer.

By applying such particles, the overgrowth and ingrowth of bone into the open-pore channels of the surface layer can be accelerated and improved. Those bioactive particles are preferably used, as mentioned previously, in the form of powders and can be applied in a sol-gel process with a water-based or silicate-based binder by means of precipitation or electrophoresis.

It is furthermore within the scope of some embodiments of the invention for at least one layer which has been applied over the virgin surface of the implant to be sintered, preferably in vacuo. In that manner it is possible, if desired, for bonding between the individual particles and between individual particles and the substrate to be improved by strengthening of the sinter neck. It should be mentioned, however, that such sintering should generally be carried out for a very brief period at the most, so as to avoid smoothing out of the microstructure of the surface coating. Usually such sintering is not necessary because of the use of the compound particles according to some embodiments of the invention, but such sintering can be used in particular cases in order to strengthen the sinter necks.

In accordance with some embodiments of the invention, a layer thickness of the surface layer in the range from 0.1 mm to 2.5 mm, preferably in the range from 0.3 mm to 1.9 mm and especially in the range from 0.5 mm to 1.5 mm is produced.

Furthermore, one problem addressed by some embodiments of the invention is solved by an implant, especially a joint replacement implant, having a surface layer including at least one layer of compound particles applied to a virgin surface of the implant by means of a vacuum plasma spraying method. The compound particles can be produced by coating or alloying of titanium particles with a sintering adjuvant or other additive that forms with titanium or an alloy thereof a eutectic that melts at a lower temperature than pure titanium.

In addition, one problem addressed by some embodiments of the invention is solved by the use of a surface layer in accordance with the disclosure herein, which is suitable, for example, for femoral stems, sockets for hip joints, femoral components for a knee joint replacement, tibial components for a knee joint replacement, components for a shoulder joint replacement, components for an elbow joint replacement, components for a toe joint replacement, components for a finger joint replacement, for a component for the fusion of vertebral bodies of the lumbar spine, for components for an intervertebral disc replacement, for transgingival implant systems, for orthodontic implant systems and tooth (replacement) implants.

As already mentioned above, the surface layer according to some embodiments of the invention is suitable for the areas of application mentioned herein, since cementless anchoring of bones to the implants is ensured by virtue of the outstanding properties of the surface layer according to some embodiments of the invention, which ensure optimized growth of bone into and over the surface layer and hence over the implant.

Further embodiments of the invention will be apparent from the disclosure herein.

BRIEF DESCRIPTION OF THE DRAWINGS

The invention will be described hereinbelow by means of example embodiments which are explained in detail with reference to the drawings, in which.

DETAILED DESCRIPTION OF THE PREFERRED EMBODIMENTS

Starting with a ground, angular titanium powder produced via the hydride stage, this can be compounded in a first step with a small quantity of a fine silicon powder. The titanium powder has in this embodiment a particle size of less than 200 µm, and the silicon powder one of 65 µm maximum. The sprayable powder or the compound particles so produced consist, as before, of preferably angular particles preferably having an axial ratio of 5:2 maximum. Next, that compounded powder is applied as an open-pore structure to the surface of the implant. The open-pore layer itself preferably has a layer thickness of from 0.5 to 1.5 mm and a porosity of from 40% to 50%. The size of the pores, determined as the maximum diameter, is preferably from 100 µm to 400 µm. The opening of those pores to the outside is preferably in the range from 150 µm to 500 µm. That layer can be applied by means of a vacuum plasma spraying method and using a simultaneous arc. The plasma spraying parameters in that method preferably are so adjusted that even though the titanium particles are caused to start to melt slightly they are only slightly compacted when they impact on the substrate, namely the virgin surface of the implant. By means of the arc used, the applied titanium particles are additionally bonded to one another, and the sinter necks connecting them and the bonding thereof to the substrate, that is, to the surface of the implant, are strengthened. A coherent network of interconnected titanium particles and, at the same time, a coherent internal porosity are obtained. This is illustrated as a metallographic microsection at 20× magnification in FIG. 6, the metal appearing light and the cavities dark.

The porosity of the titanium layer according to some embodiments of the invention applied by means of a vacuum plasma spraying method is present throughout and up to the substrate.

The geometrical measurements characterising that layer according to this embodiment of the invention are combined in the following Table summary:

| | layer thickness [µm] | porosity [%] | pore size [µm] | pore opening [µm] | sinter neck [µm] | internal surface area [µm/µm²] |
|---|---|---|---|---|---|---|
| Ti-VPS, according to one embodiment of the invention | 1120 | 46.0 ± 1.7 | 185 ± 60 | 312 ± 162 | 39 ± 16 | 0.0289 |

Figure 7:
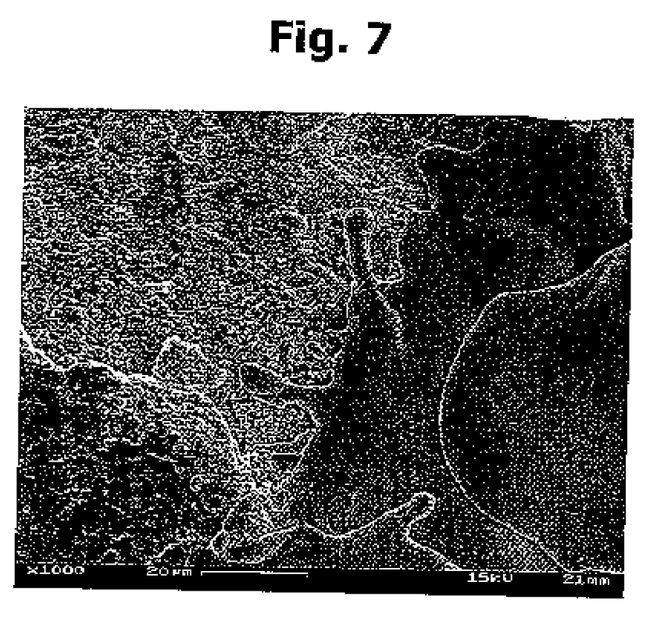
FIG. 7 is a scanning electron micrograph of the surface of a titanium particle in the vacuum plasma sprayed titanium layer according to an embodiment of the invention at 1000× magnification.

In FIG. 7, which shows a scanning electron micrograph of the surface of a titanium particle, applied according to an embodiment of the invention by means of vacuum plasma spraying, in a titanium layer according to some embodiments of the invention, it can clearly be seen that the titanium particles compounded with silicon, which form, at least in regions, a eutectic, melt only superficially, and even there only partially, during the spraying process. They retain their original geometry with axial lengths of similar size. On the other side, namely the non-melted side, the degree of roughness of the compounded titanium particles is retained. Compared with layers produced by a sintering technique, for example in accordance with U.S. Pat. No. 4,206,516, the layer according to some embodiments of the invention has a markedly greater specific surface area. A measure of the specific internal surface area is the inner boundary line measured in a metallographic microsection at 100× magnification, normalized to the detail image. The layer thickness given in the Table was determined in accordance with ASTM F 1854. The other measurements were determined by image analysis.

Figure 8:
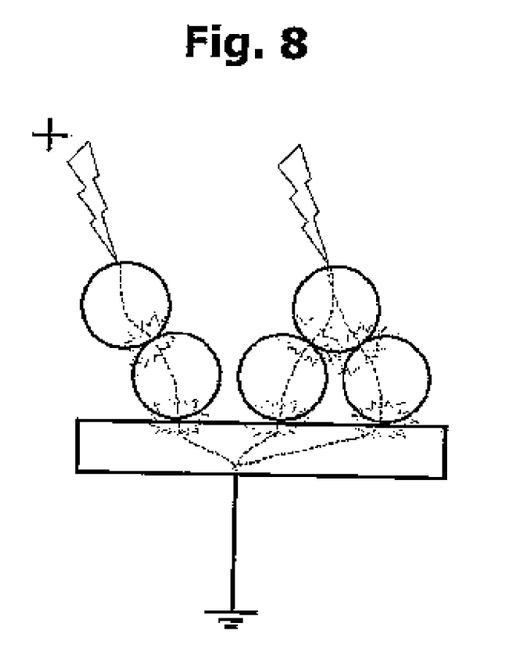
FIG. 8 is a diagrammatic illustration of the arc process according to an embodiment of the invention.

FIG. 8 is a diagrammatic illustration of an arc process used, wherein the substrate to which the particles, shown as spherical shapes, are to be applied serves as an electrode or as ground. The arc coupled into the applied particles produces at their points of connection to one another and to the substrate, which present a high contact resistance, Joule heating which causes localized sintering of those connection points to take place without the porosity and degree of roughness in the remaining regions of both the substrate and the applied particles being affected. The degree of roughness and the continuous porosity, which are optimally suited to ingrowth of bone tissue, are therefore retained in a sustainable manner, while the strength and cohesion of the particles with one another and with the substrate are improved in a sustainable manner owing to the use of the arc process.

The vacuum plasma sprayed layers, especially in combination with the arc process, exhibit a good adhesiveness to the substrate and in respect of the particles to one another, and a good shear strength within the layer. In the adhesive tensile strength test, the layer achieved values of 22.1±4.1 MPa.

The adhesiveness of individual particles was determined in a modified Miller test. That test procedure is described in ASTM G 75-01. As a modification of the ASTM standard, an abrasive suspension was dispensed with and the coated samples were drawn over the elastomer underlay (neoprene) directly and without auxiliary material, under a load of 22.4 N. The resulting abrasion of individual particles of the surfaces according to this embodiment of the invention, normalized to the porosity of the layer, is less and thus better than that of a titanium layer in accordance with the prior art. Consequently, the cohesion of the individual particles in the surface layer according to this embodiment of the invention is also better. This is due to the fact that the silicon particles applied to the titanium particles as sintering adjuvant promote specific melting of the surface and thus make possible, by means of a brief liquid-phase sintering process, a stable bonding of the particles both to the substrate and to one another.

In summary, it can be said that the method according to some embodiments of the invention for producing an open-pore biocompatible surface layer for an implant is an effective one-step process by means of which it is possible to produce a coherent pore network having a large internal surface area, good shear strength, optimized pore size and layer thickness, and high biocompatibility, which makes possible effective and rapid ingrowth and overgrowth of bone in and over an implant and which, compared with the previous state of the art, is distinctly improved in terms of its ability to enable ingrowth and overgrowth of bones, the durability of the surface layer according to some embodiments of the invention being moreover distinctly extended with the result that an implanted joint replacement can remain in the body for distinctly longer than was possible hitherto.

At this point it should be pointed out that all of the parts described above, individually and in any combination, and especially the details illustrated in the drawings, are claimed as being of inventive significance. Modifications thereof are within the purview of the person skilled in the art in view of the disclosure herein.

What is claimed is:

1. A method of producing an open-pore biocompatible surface layer for a joint replacement or other implant, said method comprising the following steps:
    coating or alloying of titanium particles with a sintering adjuvant or other additive that forms, with titanium or an alloy thereof, a eutectic that melts at a lower temperature than pure titanium, to produce compound particles;
    vacuum plasma spraying at least one layer of the compound particles onto a virgin surface of the implant to provide a surface layer on the implant; and
    producing an arc between the surface layer on the implant or another virgin surface of the implant, and a counterelectrode during and/or after said vacuum plasma spraying of the compound particles.

2. The method of claim 1, wherein the sintering adjuvant material is selected from the group consisting of silicon and cobalt.

3. The method of claim 2, wherein the sintering adjuvant comprises silicon particles in a quantity in the range from 0.5% by weight to 8.5% by weight ±1.5% by weight, silicon particles in a quantity in the range from 0.5% by weight to 3.0% by weight and silicon particles in a quantity in the range 1.0% by weight ±0.5% by weight, measured relative to the total weight of the sintering adjuvant and the titanium particles.

4. The method of claim 1, wherein an angular titanium powder having a particle size in a range selected from the group consisting of the range from 90 µm to 200 µm, and the range from 150 µm to 200 µm, is used as the titanium particles.

5. The method of claim 2, wherein silicon powder having a particle size selected from the group consisting of $\leqq 80$ µm, $\leqq 40$ µm, and $\leqq 20 \leqq$ µm is used as silicon particles.

6. The method of claim 5, wherein the particle size distribution is, in accordance with ISOIDIS 13322-1 (in percentage by volume with respect to the particle size), defined as corresponding to a 10% decile between 90 µm and 149 µm, a 50% decile between 150 µm and 229 µm, and a 90% decile between 230 µm and 330 µm.

7. The method of claim 1, wherein the titanium particles are coated with silicon particles in such a manner that the compound particles have a particle size selected from the group consisting of $\geqq 90$ µm, and $\geqq 150$ µm.

8. The method of claim 7, wherein the particle size distribution is, in accordance with ISO/DIS 13322-1 (in percentage by volume with respect to the particle size), defined as corresponding to a 10% decile between 90 µm and 149 µm, a 50% decile between 150 µm and 229 µm, and a 90% decile between 230 µm and 330 µm.

9. The method of claim 1, wherein the titanium particles are coated with silicon particles in such a manner that an angular periphery of the compound particles is substantially preserved and the compound particles have an axial ratio of $\leqq 5:2$.

10. The method of claim 1, wherein the parameters of the vacuum plasma spraying method are adjusted in such a manner that the compound particles are caused to start to melt only superficially and, on meeting the virgin surface of the implant, are only slightly compacted, so that their original geometry, especially as regards their axial ratio, is to a great extent preserved.

11. The method of claim 1, further comprising the step of coating the virgin surface of the implant with a base layer prior to or at the same time as the vacuum plasma spraying at least one layer of the compound particles onto a virgin surface of the implant step.

12. The method of claim 11, wherein the base layer comprises powder comprising material selected from the group consisting of pure titanium, titanium coated with silicon, and pure titanium and titanium coated with silicon.

13. The method of claim 11, wherein the step of coating the virgin surface of the implant with the base layer takes place in the same step as the vacuum plasma spraying at least one layer of the compound particles onto a virgin surface of the implant step, with the base layer being applied by the vacuum plasma spraying method prior to the compound particles.

14. The method of claim 11, wherein the base layer is produced with a layer thickness selected from the group consisting of $\leqq 200$ µm, $\leqq 100$ µm, and in the range from 30 µm to 50 µm.

15. The method of claim 1, wherein particles selected from the group consisting of bioactive particles, titanium dioxide bioactive particles, calcium phosphate bioactive particles, hydroxyapatite bioactive particles, tricalcium phosphate bioactive particles, and any two or more thereof are applied to the surface layer.

16. The method of claim 15, wherein the particles have a particle size in a range selected from the group consisting of the range from 0.01 µm to 5 µm, the range from 0.1 µm to 3 µm and the range from 0.2 µm to 1 µm.

17. The method of claim 15, wherein the bioactive particles are applied by means of a process selected from the group consisting of a sol-gel process, precipitation, electrophoresis, and any two or more thereof.

18. The method of claim 17, further comprising applying said bioactive particles with the assistance of a binder selected from the group consisting of water-based binder, silicate-based binder, and water-based binder and silicate-based binder.

19. The method of claim 1, wherein the at least one layer applied over the virgin surface of the implant is sintered in vacuo or otherwise sintered.

20. The method of claim 1, wherein a layer thickness of the surface layer is in a range selected from the group consisting of the range from 0.1 mm to 2.5 mm, the range from 0.3 mm to 1.9 mm and the range from 0.5 mm to 1.5 mm.

21. A method of producing an open-pore biocompatible surface layer for a joint replacement or other implant, said method comprising the following steps:
coating or alloying of titanium particles with a sintering adjuvant or other additive that forms, with titanium or an alloy thereof, a eutectic that melts at a lower temperature than pure titanium, to produce compound particles;
vacuum plasma spraying at least one layer of the compound particles onto a virgin surface of the implant to provide a surface layer on the implant,
wherein the sintering adjuvant material is selected from the group consisting of silicon and cobalt.

22. The method of claim 21, wherein the titanium particles are coated with silicon particles in such a manner that the compound particles have a particle size selected from the group consisting of $\geq 90$ μm, and $\geq 150$ μm.

23. The method of claim 22, wherein the sintering adjuvant comprises silicon particles in a quantity in the range from 0.5% by weight to 8.5% by weight ±1.5% by weight, silicon particles in a quantity in the range from 0.5% by weight to 3.0% by weight and silicon particles in a quantity in the range 1.0% by weight ±0.5% by weight, measured relative to the total weight of the sintering adjuvant and the titanium particles.

24. The method of claim 21, wherein an angular titanium powder having a particle size in a range selected from the group consisting of the range from 90 μm to 200 μm, and the range from 150 μm to 200 μm, is used as the titanium particles.

25. The method of claim 22, wherein silicon powder having a particle size selected from the group consisting of $\leq 80$ μm, $\leq 40$ μm, and $\leq 20$ $\leq$μm is used as silicon particles.

26. The method of claim 25, wherein the particle size distribution is, in accordance with ISO/DIS 13322-1 (in percentage by volume with respect to the particle size), defined as corresponding to a 10% decile between 90 μm and 149 μm, a 50% decile between 150 μm and 229 μm, and a 90% decile between 230 μm and 330 μm.

27. The method of claim 21, wherein the titanium particles are coated with silicon particles in such a manner that an angular periphery of the compound particles is substantially preserved and the compound particles have an axial ratio of $\leq 5:2$.

28. The method of claim 21, wherein the parameters of the vacuum plasma spraying method are adjusted in such a manner that the compound particles are caused to start to melt only superficially and, on meeting the virgin surface of the implant, are only slightly compacted, so that their original geometry, especially as regards their axial ratio, is to a great extent preserved.

29. The method of claim 21, further comprising the step:
coating the virgin surface of the implant with a base layer prior to or at the same time as the vacuum plasma spraying at least one layer of the compound particles onto a virgin surface of the implant step.

30. The method of claim 29, wherein the base layer comprises powder comprising material selected from the group consisting of pure titanium, titanium coated with silicon, and pure titanium and titanium coated with silicon.

31. The method of claim 29, wherein the step of coating the virgin surface of the implant with the base layer takes place in the same step as the vacuum plasma spraying at least one layer of the compound particles onto a virgin surface of the implant step, with the base layer being applied by the vacuum plasma spraying method prior to the compound particles.

32. The method of claim 29, wherein the base layer is produced with a layer thickness selected from the group consisting of $\leq 200$ μm, $\leq 100$ μm, and in the range from 30 μm to 50 μm.

33. The method of claim 21, wherein particles selected from the group consisting of bioactive particles, titanium dioxide bioactive particles, calcium phosphate bioactive particles, hydroxyapatite bioactive particles, tricalcium phosphate bioactive particles, and any two or more thereof are applied to the surface layer.

34. The method of claim 33, wherein the particles have a particle size in a range selected from the group consisting of the range from 0.01 μm to 5 μm, the range from 0.1 μm to 3 μm and the range from 0.2 μm to 1 μm.

35. The method of claim 33, wherein the bioactive particles are applied by means of a process selected from the group consisting of a sol-gel process, precipitation, electrophoresis, and any two or more thereof.

36. The method of claim 35, further comprising applying said bioactive particles with the assistance of a binder selected from the group consisting of water-based binder, silicate-based binder, and water-based binder and silicate-based binder.

37. The method of claim 21, wherein the at least one layer applied over the virgin surface of the implant is sintered in vacuo or otherwise sintered.

38. The method of claim 21, wherein a layer thickness of the surface layer is in a range selected from the group consisting of the range from 0.1 mm to 2.5 mm, the range from 0.3 mm to 1.9 mm and the range from 0.5 mm to 1.5 mm.

39. The method of claim 21, wherein the titanium particles are coated with silicon particles in such a manner that the compound particles have a particle size selected from the group consisting of $\geq 90$ μm, and $\geq 150$ μm.

40. The method of claim 39, wherein the particle size distribution is, in accordance with ISO/DIS 13322-1 (in percentage by volume with respect to the particle size), defined as corresponding to a 10% decile between 90 μm and 149 μm, a 50% decile between 150 μm and 229 μm, and a 90% decile between 230 μm and 330 μm.

* * * * *